(12) United States Patent
Meyer et al.

(10) Patent No.: US 10,299,047 B2
(45) Date of Patent: May 21, 2019

(54) TRANSPARENT HEARING AID AND METHOD FOR FITTING SAME

(71) Applicant: Meyer Sound Laboratories, Incorporated, Berkeley, CA (US)

(72) Inventors: John D. Meyer, Berkeley, CA (US); Toban A. Szuts, El Cerrito, CA (US)

(73) Assignee: Meyer Sound Laboratories, Incorporated, Berkeley, CA (US)

( * ) Notice: Subject to any disclaimer, the term of this patent is extended or adjusted under 35 U.S.C. 154(b) by 0 days.

(21) Appl. No.: 15/693,319

(22) Filed: Aug. 31, 2017

(65) Prior Publication Data

US 2017/0366903 A1    Dec. 21, 2017

Related U.S. Application Data

(63) Continuation-in-part of application No. 14/851,371, filed on Sep. 11, 2015, which is a continuation of
(Continued)

(51) Int. Cl.
*H04R 25/00* (2006.01)
*A61N 1/36* (2006.01)

(52) U.S. Cl.
CPC ....... *H04R 25/353* (2013.01); *A61N 1/36038* (2017.08); *H04R 25/50* (2013.01);
(Continued)

(58) Field of Classification Search
CPC .... H04R 25/353; H04R 25/50; H04R 25/505; H04R 25/02; H04R 25/652; H04R 25/656; H04R 2225/025; H04R 2460/09
(Continued)

(56) References Cited

U.S. PATENT DOCUMENTS

| 4,475,230 A | 10/1984 | Fukuyama et al. |
| 5,706,352 A | 6/1998 | Engebretson et al. |

(Continued)

FOREIGN PATENT DOCUMENTS

WO    PCT/US13/55004    2/2014

OTHER PUBLICATIONS

George J. Frye, Testing Digital and Analog Hearing Instruments: Processing Time Delays and Phase Measurements A Look at Potential Side Effects and Ways of Measuring them, reprinting from The Hearing Review, Oct. 2001.
(Continued)

*Primary Examiner* — Ahmad F. Matar
*Assistant Examiner* — Sabrina Diaz
(74) *Attorney, Agent, or Firm* — Beeson Skinner Beverly, LLP (57) ABSTRACT

The hearing aid includes a signal processor having a level-dependent filter section and a level-independent filter section. The level-dependent filter section provides level-dependent gain wherein sound is attenuated or amplified depending on the level of the incoming sound. The level-independent filter section provides substantially constant gain wherein sound that passes through the filter section is not changed in level, and provides transparency in that it corrects for insertion loss caused by the earpiece of the hearing aid when worn by the user. The level dependent and level independent filter sections, when fitted to the user, greatly improve the user's perception of sound.

7 Claims, 8 Drawing Sheets

Related U.S. Application Data application No. 13/967,271, filed on Aug. 14, 2013, now Pat. No. 9,154,889, application No. 15/693,319, which is a continuation-in-part of application No. 15/204,933, filed on Jul. 7, 2016, now Pat. No. 9,769,575, which is a continuation of application No. 14/552,362, filed on Nov. 24, 2014, now Pat. No. 9,392,366.

(60) Provisional application No. 61/683,668, filed on Aug. 15, 2012, provisional application No. 61/908,668, filed on Nov. 25, 2013.

(52) U.S. Cl.
CPC ........... *H04R 25/505* (2013.01); *H04R 25/70* (2013.01); *H04R 2225/025* (2013.01); *H04R 2460/05* (2013.01); *H04R 2460/09* (2013.01)

(58) Field of Classification Search
USPC .................... 381/312, 328, 322, 321, 381
See application file for complete search history.

(56) References Cited

U.S. PATENT DOCUMENTS

| | | | |
|---|---|---|---|
| 5,903,655 A * | 5/1999 | Salmi | H04R 25/356 381/312 |
| 6,108,431 A | 8/2000 | Bachler | |
| 7,372,969 B2 | 5/2008 | Roeck | |
| 7,474,758 B2 | 1/2009 | Beck et al. | |
| 8,036,405 B2 | 10/2011 | Ludvigsen et al. | |
| 8,213,653 B2 | 7/2012 | Von Buol et al. | |
| 2007/0263891 A1 | 11/2007 | Von Buol et al. | |
| 2016/0150330 A1* | 5/2016 | Niederberger | A61F 2/08 381/314 |
| 2017/0208382 A1* | 7/2017 | Grinker | G10K 11/1784 |

OTHER PUBLICATIONS

Frye, George J., Understanding the ANSI Standard as a Tool for Assessing Hearing Instrument Functionality, Comparing the new ANSI S3.22 2003 standard to its 1996 predecessor, The Hearing Review, May 2005.

Schum, Donald J., The Audiology in Agil, AudiologyOnline, Apr. 19, 2010.

Moore, Brian C. J., Cochlear Hearing Loss, Psyciological, Psychological and Technical Issues Second Edition, 2007, pp. 240-241, John Wiley & Sons Ltd., West Sussex, England.

Muse Kastanovich, Pass Labs Aleph 3 power amplifier, Datasheet [online], Stereophile, Apr. 29, 1997, Paragraph 5, Retrieved from the Internet, <URL: http://www.stereophile.com/solidpoweramps/674>.

P. White, Advanced Gating Techniques, Part 1, Datasheet [online], Sound on Sound, Apr. 2001, Paragraph 6, Retrieved from the Internet, <URL: http//www.soundonsound.com/sos/apr01/articles/advanced.asp>.

\* cited by examiner

TRANSPARENT HEARING AID AND METHOD FOR FITTING SAME

CROSS-REFERENCE TO RELATED APPLICATIONS

This application is a continuation in-part of U.S. Non-Provisional patent application Ser. No. 14/851,371 filed Sep. 11, 2015, now pending, which is a continuation of U.S. Non-Provisional patent application Ser. No. 13/967,271 filed Aug. 14, 2013, now U.S. Pat. No. 9,154,889 issued Oct. 6, 2015, which claims the benefit of U.S. Provisional Patent Application No. 61/683,668 filed Aug. 15, 2012, and a continuation in-part of U.S. Non-Provisional patent application Ser. No. 15/204,933 filed Jul. 7, 2016, now pending, which is a continuation of U.S. Non-Provisional patent application Ser. No. 14/552,362 filed Nov. 24, 2014, now U.S. Pat. No. 9,392,366 issued Jul. 12, 2016, which claims the benefit of U.S. Provisional Patent Application No. 61/908,668 filed Nov. 25, 2013. The foregoing applications are incorporated herein by reference.

BACKGROUND

The present invention generally relates to hearing aids and more particularly relates to a hearing aid that improves the hearing experience and to a method for fitting such a hearing aid to a user of the hearing aid.

Hearing aids typically consist of a microphone, a signal processor, and a loudspeaker (sometimes called a "receiver" or "output transducer"). The loudspeaker directs sound picked up by the microphone and processed by the signal processor into the ear canal and is held in place using an earpiece that fits in the ear canal. The earpiece changes the acoustic environment of the ear drum and therefore the perception of sound in the same way that a mute inserted into the bell of a trumpet changes its timbre. In general, an earpiece will attenuate at least some frequencies from the sound incident on the ear drum. This phenomenon is often called the "insertion effect".

An earpiece that does not completely block the ear canal is said to be an open earpiece. Usually this style of earpiece is accomplished using several cross-sectional holes in a thin and light-weight earpiece. As a result, there is an open-air path for sound to travel to the ear drum, which allows some frequencies, usually lower ones, to reach the ear drum with no attenuation. Higher frequencies tend to be blocked by the earpiece and are therefore moderately attenuated. Overall, in instances where an open-ear earpiece is used, the insertion effect affects only a portion of the audible bandwidth.

An earpiece that completely blocks the ear canal, usually with a heavy plastic or silicon earpiece mold, is said to be a closed earpiece. In a closed earpiece, there is no air-conduction path for sound to travel directly to the ear drum and thus all sound frequencies are severely attenuated. This attenuation allows the hearing aid to provide more gain before feeding back to the input microphone. However, blocking the entirety of the external portion of the ear canal causes the user's own voice to resonate in the closed cavity, amplifying the low frequency harmonics. This "head in a barrel" effect, sometimes called the occlusion effect, can be mitigated in part by introducing a vent through the earmold. The larger the diameter of the vent, the more the occlusion effect is reduced. However, this vent has the disadvantage of reducing the earmold's attenuation at lower frequencies and thus the additional gain that a closed-ear earpiece can provide at those frequencies.

The natural resonance of the ear depends on ear shape, which varies considerably between individuals. As a result, the exact insertion effect caused by an earpiece differs from person to person. This variability in the insertion effect is why earpieces are generally custom molded for an individual's unique ear shape and is why a fitting process is needed to compensate for an individual's unique insertion effect.

A typical hearing aid works by providing frequency dependent amplification, or gain. More recent developments have provided improvements to typical hearing aids by introducing gain that not only depends on frequency but also on level. In either case the gain needs to be tuned to match the user's particular hearing loss for each ear and this is done in a process referred to as "fitting."

Many known fitting processes have been developed by hearing aid manufacturers and academic research groups. These fitting processes are generally oriented toward a multiband architecture where there is minimal frequency overlap between bands and generally ignore the potential artifacts that come from phase distortion and combination effects.

One such artifact results from the latency of the hearing aid, that is, the time delay between when a sound is sensed at the microphone and when it is converted to an acoustical sound wave at the hearing aid's loudspeaker. For modern digital hearing aids, the latency is between 3-7 milliseconds. Older analog hearing aids had a latency around 1-2 milliseconds. When both the incident sounds perceived by the ear drum and amplified sounds produced by the hearing aid are similar in sound level, any non-zero latency of the hearing aid causes comb filtering, a form of spectral distortion. Comb filtering is characterized by a series of regularly spaced spectral peaks and dips in the sound pressure at the ear drum. For longer latencies, the first dip is at a lower frequency and hence a larger portion of the frequency spectrum is affected. Shorter latencies produce less extensive comb filtering. The human ear is very sensitive to this kind of artifact. Latencies shorter than 8 milliseconds are perceived as tone coloration, while longer latencies can be perceived as echoing, beating, or tone coloration, depending on the relative loudness of the delayed sound.

Another recombination artifact arises from phase distortion in the amplified sound. This also produces a structure of spectral dips and peaks. Frequencies that are 180 degrees out of phase recombine destructively, creating a dip, while frequencies that are in phase add constructively, creating a peak. Since phase distortions are often spread non-uniformly over the frequency spectrum, this kind of artifact potentially affects less of the spectrum than latency artifacts. Phase distortion caused by summation is greatest when the direct sound is as loud as the amplified sound. The source of phase distortion can be any component in the signal path including the microphone, signal processing components, or the loudspeaker. Recent evidence suggests that phase is used by humans for many hearing tasks, including source localization, speech encoding, and detection of phase modulation.

The present invention provides a means for a hearing aid and a method of fitting a hearing aid to a user that both avoids the coloration that results from an altered ear canal resonance (i.e., the insertion effect) as well as the artifacts caused by level-dependent gain. The hearing aid with either open or closed earpieces, when fitted in accordance with the invention, can provide the user with a much more "natural" or "transparent" perceived sound. The invention provides an earpiece that is transparent after it has been fitted. By providing transparency, the user's hearing loss can be more effectively corrected.

SUMMARY OF INVENTION

The present invention involves a hearing aid and method of fitting a hearing aid to a user such that at low sound levels the user hears amplified sound while at higher sound levels the user hears sound perceived as "natural" or "transparent" but which is not amplified. The hearing aid comprises a microphone that converts incoming sound to an electrical signal, a signal processor that acts on the electrical signal, and a loudspeaker that converts the processed electrical signal back into sound in the user's ear canal. The signal processor includes at least two filter sections, a level-dependent filter section and a level-independent filter section. The level-dependent filter section provides level-dependent gain wherein sound processed by this section is attenuated or amplified depending on the level of the incoming sound. The level-independent filter section on the other hand provides substantially constant gain wherein sound that passes through the filter section is not changed in level. These filter sections provide separate electronic paths through which incoming sound can reach the user's eardrum. The path provided by the level-dependent filter section is referred to herein as the "level-dependent path" or "LD path," and the path provided by the level-independent filter section is referred to herein as the "level-independent path" or "LI path."

When the earpiece is in place, any path through which non-amplified sound reaches the eardrum is referred to herein as the "transparency path." In the case of an open earpiece, the transparency path includes both a direct acoustic sound path through openings in the earpiece and through which incoming sound reaches the eardrum directly ("direct sound"). In addition to this path, the transparency path includes the electronic LI path through the signal processor. The LI path corrects for the insertion effect of the open earpiece but otherwise does not substantially affect the sound level passing through this path. In closed earpieces, any direct acoustic sound is greatly attenuated by the earpiece. Thus, in closed ear devices, the non-amplified sound arriving at the eardrum contributes negligibly to the perceived sound, and so the transparency path is provided almost entirely by the signal processor.

In regards to the transparency path, the fitting method produces a path that is the most "natural" or "transparent" to the user, that is, a path that best compensates for the insertion effect of the earpiece. Transparency can most suitably be achieved subjectively, based on what the user perceives as natural. For example, different parameters can be provided for the user to choose which produces the most natural results. Alternatively, an audiologist or other fitting assistant can iteratively adjust the parameters in response to feedback from the user. These steps are performed at sufficiently loud sound input levels that the user can hear normally without the hearing aid.

The level-dependent path is provided entirely by the signal processor of the hearing aid and particularly by the level-dependent section of the signal processor. In this path, sounds that are below a certain sound threshold level (generally referred to as "low level sounds") are amplified above the threshold. For a person with hearing loss this could be sounds below a user's tone detection threshold (also referred to as threshold of audibility). In such cases the level-dependent filter section amplifies the sound above the user's threshold of audibility (as determined by a hearing test) to compensate for the hearing loss. This level-dependent amplification process is referred to herein as "threshold compensation."

The present invention provides a number of benefits. By attenuating the amplified sound at a threshold such as the user's threshold of audibility, the hearing aid's loudspeaker does not need to provide gain at loud output levels, which reduces the dangers of clipping and the need for a limiter. Both limiters and clipping introduce harmonic distortion in the amplified signal; limiters do so by design, to avoid the more extreme artifacts caused by clipping, which is the excitation of nonlinear modes in the diaphragm. However, because the LD path has constant gain, the loudspeaker still needs be able to produce output level equal to the incident sound level. Depending on the source, these could be quite high, as (instantaneous) peak levels greater than 120 dB SPL are not uncommon.

Furthermore, the invention will increase the number and quality of spatial cues available to the user. Such cues result from the complete head-related transfer function, which is shaped by the external ear anatomy (pinna and concha), the ear canal, and binaural effects caused by the head (such as interaural loudness, timing, and phase differences). Whenever a frequency is amplified, latency and phase distortions are necessarily introduced at that frequency and natural cues are perturbed. The invention, and particularly the level-dependent feature of the invention, preserves natural cues by judicious amplification of incident sound.

On a more general level, the invention improves sound quality perceived by the user while preserving natural cues, so that the hearing aid is less taxing for the user. In complex auditory environments, the brain can use multiple cues to separate sound sources and direct auditory attention. In many cases, loss of such cues results in reduced comprehension or intelligibility. However, recent studies have shown that loss of certain cues may also increase the cognitive effort required to maintain the same performance (Sarampalis, et al., "Objective Measures of Listening Effort: Effects of Background Noise and Noise Reduction", Journal of Speech, Language, and Hearing Research, Vol 52:1230-1240, 2009). This is shown most succinctly by giving the test subject a second, non-auditory task to perform along with the primary auditory task. With hearing loss, degraded input quality, or other factors that increase cognitive load, performance on the second task will drop dramatically and the subject will fatigue much more quickly than normal.

Other aspects and benefits of the invention will be apparent from the description and claims which follow.

DESCRIPTION OF THE ILLUSTRATED EMBODIMENT

While components of the hearing aid described herein are illustrated and described as being implemented by digital signal processing techniques, it will be appreciated that such components could instead be implemented by analog circuits. Also, while the invention is described herein as being related to a hearing aid, the invention is not intended to be limited to hearing aids used solely to correct for hearing loss. The invention could also be used in connection with hearing assist devices that do not compensate for hearing loss such as products known as PSAPs (personal sound amplification products).

Also, when referring to sound as being "amplified," it is meant that the signal processor provides a gain that is greater the zero. Gain less than zero results in sound being attenuated.

Figure 1:
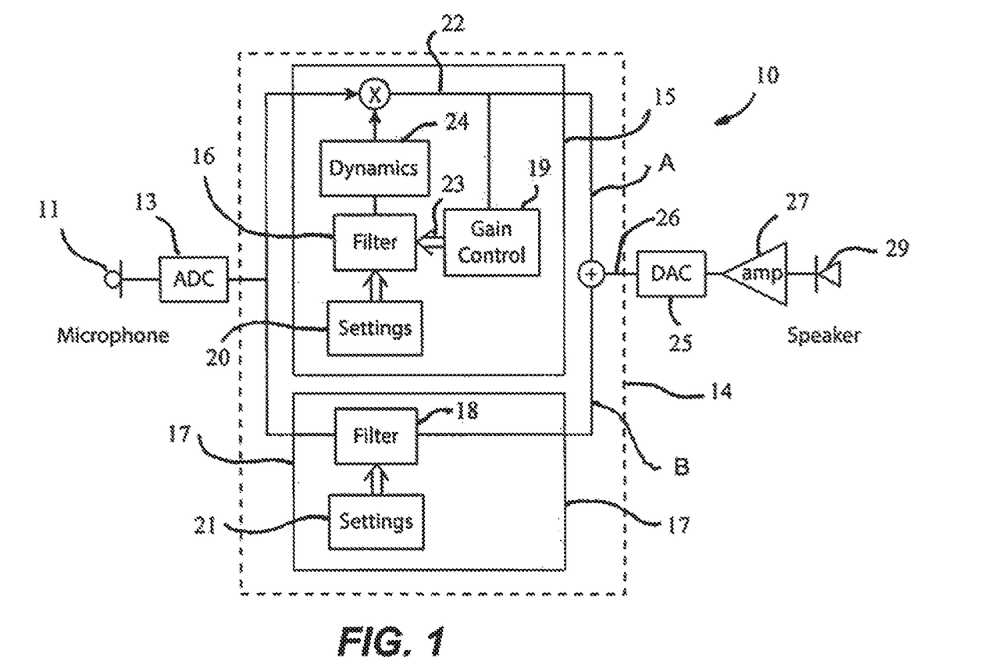
FIG. 1 is a functional block diagram representation of a hearing aid in accordance with the invention.

Referring now to the drawings, FIG. 1 illustrates in block diagram form an embodiment of a hearing aid 10 having sound pick-up means, suitably microphone 11, which converts incoming (incident) sound to an electrical audio signal that can be digitized by an analog-to-digital converter 13 for subsequent processing by a signal processor 14. The signal processor includes a level dependent (LD) filter section 15 having an output denoted in FIG. 1 by the letter A and a level-dependent filter 16 that provides a level-dependent path for the electrical audio signal, in this case digitized electrical audio signal. By "level-dependent," it is meant that the level of the audio signal that emerges at A depends on the level of the incoming sound. The signal processor additionally includes a level-independent (LI) filter section 17 having an output denoted in FIG. 1 by the letter B and a filter 18 that provides a level-independent or "linear" path for the same incoming signal. By "level-independent," it is meant that the gain of the audio signal through this section does not depend on the level of the incoming sound.

As later described in more detail, the LD filter section provides level and frequency dependent gain (LD gain) that achieves a desired threshold compensation (TC), that is, for low level sounds below a selected sound threshold the sounds will be amplified such that they are above the threshold. Where it is desired to correct for a user's hearing loss, the selected threshold would preferably be the user's threshold of audibility and the LD filter section would have a specific frequency response that best compensates for the hearing loss. The LD filter section can include other functional blocks, such as a gain control block 19 and a dynamics block 24 for controlling the time course of gain changes. A system and method of providing level dependent gain for threshold compensation with dynamic control in an open ear hearing device is described in applicants' U.S. Pat. No. 9,154,889. (This same system and method can also be used with closed ear devices).

The gain of the LI filter section on the other hand is not level dependent: its constant gain is independent of level, but may depend on frequency. Gain provided by the LI filter section corrects for the insertion loss of the ear piece in the user's ear canal. Correcting for insertion loss reduces the acoustic effect of the ear piece in the ear to provide "transparency." A detailed approach to correcting for insertion loss is described in applicants' U.S. Pat. No. 9,392,366.

For the level dependent and independent paths of the signal processor 14, the respective filter settings (shape, bandwidth, gain structure, etc.) are controlled within each section by the settings blocks 20 and 21, respectively. The signal processor can be provided with a settings mode that allows for switching between different filter settings. For the LD filter, the filter settings would be established that achieve a desired threshold compensation for a user; for users with hearing loss the desired threshold compensation would be based on the user's particular hearing loss characteristics. For the LI filter, the filter settings would be established based on the geometry of the ear piece and the resulting insertion loss caused by the ear piece. All such settings can be computer controlled, or as described later could be presets that are actuated (recalled) by the user.

As represented by gain control block 19, the gain supplied by the hearing aid can be determined from the LD filter's output signal at gate output 22 in a feedback configuration, and can be used to modify the amplitude of the filter as represented by feedback arrow 23. It will be appreciated that gain control could be implemented in ways other than described above, for example, using a feed-forward architecture.

After the outputs A and B from respective processor sections 15 and 17 are summed, the combined output signal 26 can then be converted to an analog signal by a digital-to-analog convertor 25, amplified by an amplifier 27, and passed to a loudspeaker 29. Most suitably, microphone 11 (input transducer) and loudspeaker 29 (output transducer) will reproduce the audio signal accurately without adding spectral or phase distortion. This requires linear transducers that have a flat phase response and minimal harmonic distortion up to the highest output level required.

Figure 2:
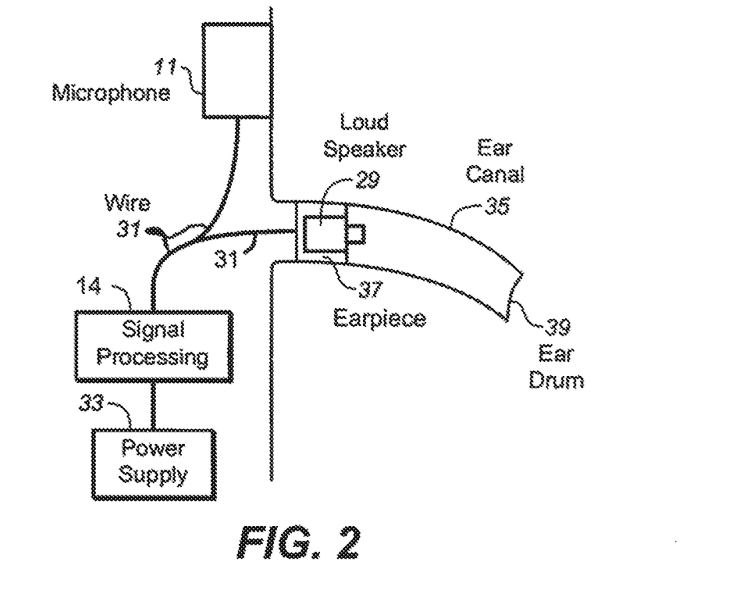
FIG. 2 is a graphical representation of the physical components for the hearing aid represented in FIG. 1, including component placement both outside and inside the ear canal.

FIG. 2 pictorially represents a placement of the physical components of the hearing aid shown in FIG. 1 in relation to a human ear. The physical components are comprised of a microphone 11, a signal processor component 14, a power supply 33 such as a battery or battery pack, and an earpiece comprised of an ear mold 37 and embedded loudspeaker 29, which is positioned in the user's ear canal 35. While the signal processor 12 and microphone 11 are shown as separate components, it is contemplated that they can be housed together in a single wearable unit. The power supply can likewise be housed together with the signal processor, or may be located separately and attached to the circuit by a wire as shown. Wires 31 connect microphone 11 to the signal processor 14 and the signal processor to the loudspeaker 29. While loudspeaker 29 is most suitably held in the ear canal by the earpiece, but it could also be supported elsewhere as long as its acoustic output is conveyed to the ear canal. The earpiece is considered an open-ear design if it doesn't entirely block the ear canal, such that over some frequency range the incoming sound can pass through the ear canal directly to the eardrum 39 (direct sound) without appreciable attenuation. The earpiece is considered a closed-ear design if the ear canal is completely blocked and direct sound is significantly attenuated at all or most frequencies. It is also contemplated that the earpiece could be eliminated altogether by stimulating the cochlea through means other than an air-pressure wave at the ear drum, such as by driving the components of the middle ear directly, or using a cochlear implant to electrically stimulating neurons in the cochlea. One skilled in the art could readily apply this invention to such alternate ways of stimulating the cochlea.

Figure 3:
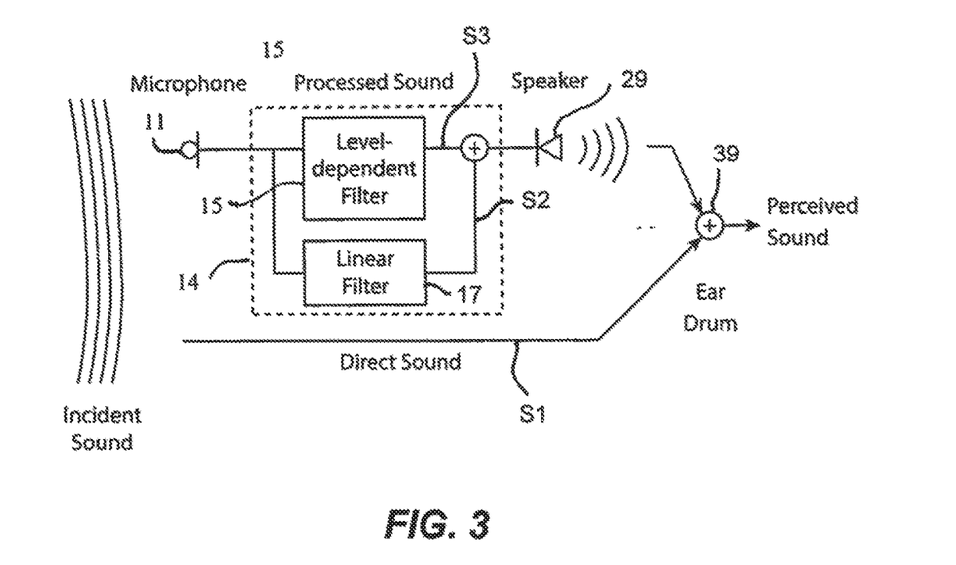
FIG. 3 is a graphical representation of the paths taken by sound as it passes to the eardrum of a person fitted with the hearing aid of FIGS. 1 and 2.

FIG. 3 illustrates how sound reaches the ear drum 39 when using the above described hearing aid. The sound at the ear drum consists of three components S1, S2, and S3, corresponding to the different paths the sound travels. All sum together to create the final perceived sound 41 at the ear drum.

The first component is the direct sound S1, which is any sound that bypasses the hearing aid and reaches the ear drum 39 directly. For an open-ear device, this path is significant, especially at low frequencies. For a closed-ear device, this path is considerably attenuated, sometimes by as much as 30 or 40 dB, and can usually be neglected. The direct sound S sums acoustically with the amplified sound 45 produced by loudspeaker 29.

The second component S2 is produced by the LI filter section 17 and follows the LI path of the LI filter section. Because this filter is linear and has constant gain, it can be grouped with the direct sound 43; their sum is the "transparency sound" that corrects for the insertion effect of the earpiece.

The third component S3 is produced by the LD filter 15 and follows the LD path of the LD filter section. S3 provides additional gain at low levels to correct for the user's hearing loss and is referred to herein as "amplified sound"; it brings low level sounds above the desired sound level threshold, which when correcting for hearing loss is the threshold at which the user begins to hear sounds (i.e. the threshold of audibility). S2 and S3 are summed digitally (or electrically) inside the signal processor, and are referred to collectively as the "processed sound." The processed sound signal is then converted to acoustical sound by the output transducer 29.

It will be appreciated that, while the above-described signal is shown as having a single LD path and a single LI path summed in parallel, the processor could have multiple LD filter sections and/or multiple LI filter sections providing multiple LD and/or LI paths summed in parallel.

As mentioned above, the frequency response of the processed sound is determined by the filter settings, which can be controlled by an external computer. Each filter, whether in the LD or LI path, can be thought of as an equalization curve, applying gain separately to narrow bands of frequency. The shape of each filter can be highly customizable. For instance, a filter may be flat across all frequencies, boosted at particular frequencies (high-pass, low-pass, or band-pass), or bimodal (peaking at two frequencies). In addition to amplitude, filters will also have a phase component that affects the output signal: this can be minimal for a judicious choice of filter, or can be extreme for other types. The phase response is perceptually important and can play an important role in a transparent fitting.

The method of fitting the above-described hearing aid to a user where it is desired to correct for the user's particular hearing loss involves adjusting the filter settings to the user's ear geometry and hearing loss characteristics. This is done in two fundamental fitting steps: (i) setting the linear (transparency) filters and (ii) setting the threshold-compensation filters with level-dependent gain. The steps can be done in either order.

Figure 4:
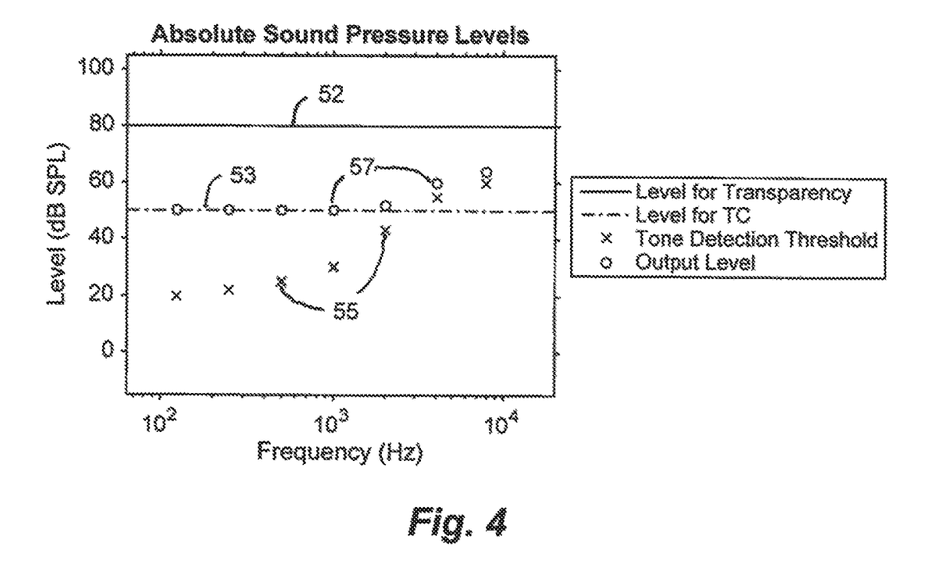
FIG. 4 shows the sound levels used for the transparency and threshold compensation fittings, how they relate to a user's tone detection threshold, and the output sound level of the device.

The fitting method can best be described in reference to FIG. 4, which shows the tone detection threshold for a hypothetical case of mild hearing loss above 2000 Hz. The person's tone detection threshold as a function of frequency is represented by a series of data points 55. This threshold is determined by a standard hearing test that measures how loud a pure tone (or single frequency sinusoid) must be for a 50% chance of detection. However, thresholds can be chosen other ways (75% detection threshold, speech detection threshold, etc.) The tone detection threshold is sometimes called the audiometric threshold, and its graph may be called the audiogram.

Each step of the fitting method is performed with a different input signal level, which depends on the user's tone-detection threshold. For the fitting of the LI (linear) filter, the test signal level should be significantly above the tone-detection threshold 55 across all frequencies, for example between 100 Hz and 10,000 Hz. That is the test signal level should be loud enough that all frequencies are audible to the user. In FIG. 4, this test signal level is set at 80 dB, as represented by 52. Care should be taken not to set this test signal too loud as it could damage the hearing of the person being fitted. Generally, it is recommended that test signals be below 100 dB SPL.

When fitting the LD filters to achieve threshold compensation, the test signal level must be below the tone detection threshold of at least one frequency band, or possibly below for all bands. In FIG. 4 this level is nominally set at 50 dB SPL as represented by 53. In general, the input level should be above 20 dB SPL and/or the level at which speech can be understood.

Also shown in FIG. 4 are the loudspeaker's target output levels 57, which are specific to the hypothetical hearing loss shown here. Below about 2000 Hz, the output levels are identical to the input signal, which means that the device output comes solely from the transparency components (S1 and S2 in FIG. 3). However, for frequencies above 2000 Hz, contributions from the LD filter appear in the form of amplified sound or additional gain. The LD filter applies more gain when the tone detection threshold is louder.

Figure 5A:
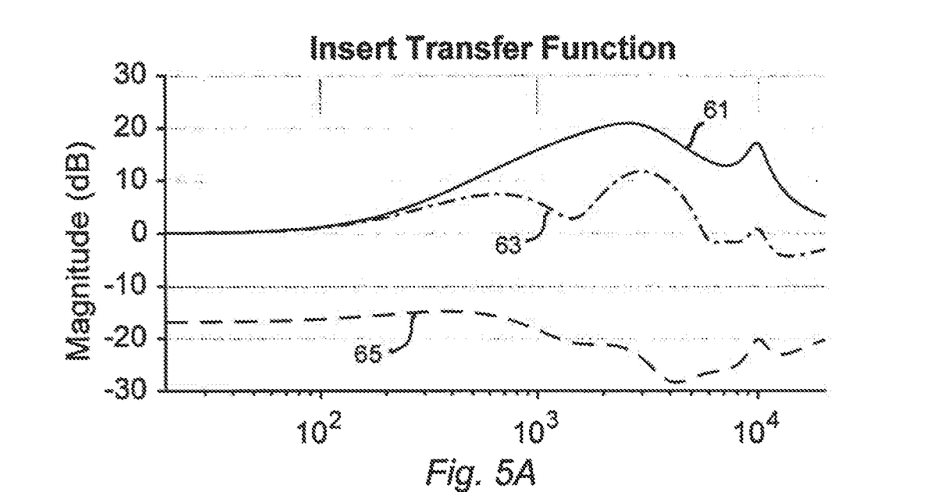
FIGS. 5A and 5B show the transfer function (magnitude and phase as a function of frequency) of the sound paths in a representative human ear without any earpiece in the ear canal (normal), with an open earpiece, and with a closed earpiece.
Figure 5B:
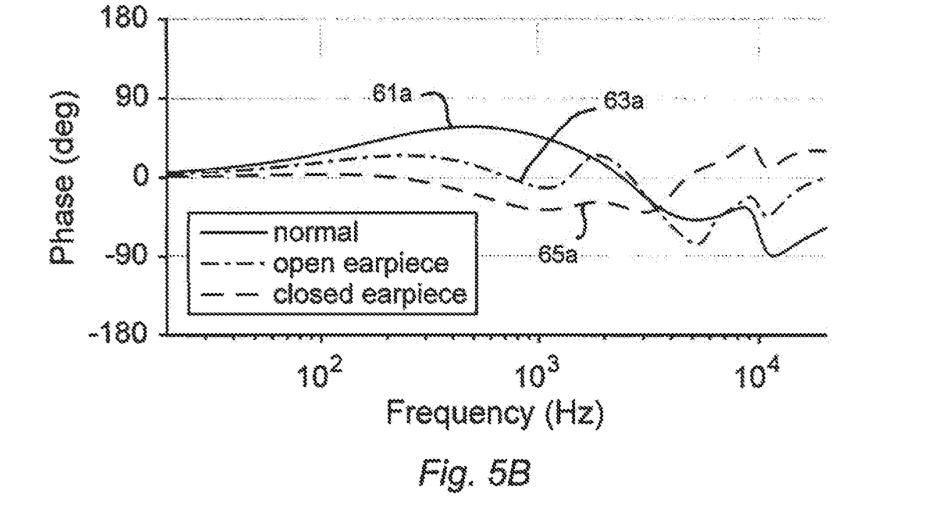

FIGS. 5A and 5B show how an earpiece affects the transfer function between the sound source (located some distance away from the head) and the ear drum. When an earpiece is present, the transfer function is called the insert transfer function. The hearing aid device of the invention compensates for this effect to achieve a natural or transparent perceived sound.

FIG. 5A shows how an earpiece in the ear canal attenuates the transfer function magnitude. A transfer function through the ear canal without an earpiece, denoted by curve 61, represents transparency. Upon inserting an open earpiece into the ear canal, the transfer function 63 is attenuated at frequencies above about 300 Hz. At low frequencies where there is no change, the sound energy is conveyed by the direct sound path that goes through the openings in the earpiece. At frequencies above 300 Hz, the difference in magnitude depends on frequency and is relatively small: in this example, the attenuation is about −5 to −15 dB, but it is greatest at 1.2 kHz and less at 3 kHz. For a closed-ear device 65, however, there is a broad-band attenuation in gain across all frequencies. In this example, attenuation is roughly 15 dB at low frequencies. For higher frequencies, attenuation varies slightly and is as high as 40 dB.

The phase component of the insertion transfer function is shown in FIG. 5B. The phase effects are constrained to areas with a different magnitude shape—above about 100 Hz for both types of earpiece.

The insertion effect is compensated for by adjusting the LI filter settings so that the summation of paths S1 and S2 results in a transfer function as close as possible to the normal transfer function represented by curves 61 and 61a in FIGS. 5A and 5B, respectively. Since the transfer function is linear, it can be described completely by the linear combination of the linear filter and direct paths. The adjustments can be achieved in different ways: the transfer functions can be measured directly with a small probe microphone and used to calculate the proper filter settings mathematically, or the needed adjustments can be determined subjectively.

For subjective adjustments, the user can compare the sound perceived without an earpiece to sound perceived with an earpiece and transparency filter. Based on the user's feedback, the settings can be adjusted until both are perceived as identical. The signal used could be music, speech, or test signals such as pink noise or pure tones, depending on the preferences of the user. Alternatively, the user could listen to different pre-established filter settings ("presets") and simply choose the one that sounds most natural or comfortable. Such presets could be recalled in a variety of ways, such as voice activation or control elements on a touch screen housed and communicating with the signal processor. While selecting between filter presets may not be as accurate as the other more precise approach described above, it is considerably faster and requires far fewer technical judgements. In establishing the transparency setting, it is contemplated that both the magnitude and phase response of the occluded ear canal will be corrected.

The shape of the linear LI filter depends on the geometry of the user's ear, the geometry of the earpiece, and the exact placement of the microphone. Most importantly, since ear geometry differs significantly between people, there exists no setting that's optimal for a majority of people. Earpiece geometry includes whether the ear tip is open or closed, as well as the depth of insertion and the presence and properties of an earmold vent. Also, the insertion effect will be less pronounced if the microphone is located at the entrance of the external ear canal, and more pronounced when positioned behind the user's pinna. Furthermore, a microphone positioned behind the user's pinna will result in a transfer function missing certain features normally used to determine sound source location, such as resonances caused by the concha. While not ideal, having a microphone distant from the ear canal can be dealt with by prioritizing the transfer function from frontal positions, since a person usually faces the sound source being attended to.

In correcting for hearing loss, threshold compensation (TC) is required to bring inaudible frequencies above the threshold of each user's particular hearing. This is achieved by adjusting the level-dependent filter settings represented by block 20 in filter section 15. For one frequency band, as the input level (incoming sound level) increases, the filter gain is gradually attenuated until the level of the LD path drops below the level of the transparency path (S1 and S2 in FIG. 3). At that point, the transparency sound becomes perceptually dominant. The gain can be attenuated in such a way that the phase response also gradually decreases to zero.

The precise filter characteristics needed to compensate for the hearing loss for a particular individual can be referred to as a "fitting."

Thus, at low input levels, the LD filter is tailored to the user's particular measured hearing loss. For inputs below the detection threshold, sounds need to be amplified enough that they are brought above threshold so they are audible. For incoming sound inputs at and above the detection threshold, the output sound should give way to the transparency sound in a controlled manner. The exact level at which this happens depend on how quickly the user's equal-loudness contours return to normal values.

At intermediate input levels, the LD path combines with the transparency path (that is, the LI path and any direct sound) to produce an intermediate output sound level. If the filter remains active too far above the threshold of audibility, the resulting sound is heard as too loud and unpleasant to the user: the perception can be bright or boomy, depending on the type of hearing loss and the hearing band under consideration. In this 'crossover' regime where the amplified and the transparency are at similar levels, the phase response is important, since any phase shifts could lead to large cancellations or peaks in the frequency response. As the contribution of the LD filter diminishes above the user's threshold, the phase effects are reduced. One way to ensure an appropriate phase response is by using minimum phase filters, which alter phase only at those frequencies that are also amplified.

Like the LI filter settings, the settings for the LD filter section can be established subjectively by having the user could listen to different pre-established filter settings or presets for the LD filter and simply choose the one that sounds most natural or comfortable. And again, such presets could be recalled in a variety of ways as described above in connection with presets for the LI filter. Furthermore, the presets for the LD and LI filter could be combined into a single set of presets where, by selecting between presets, the user is allowed to choose the preset that sounds most natural or comfortable to the user. In the case of user having hearing loss a preset can be selected which gives the user a more normal hearing experience.

Figure 6:
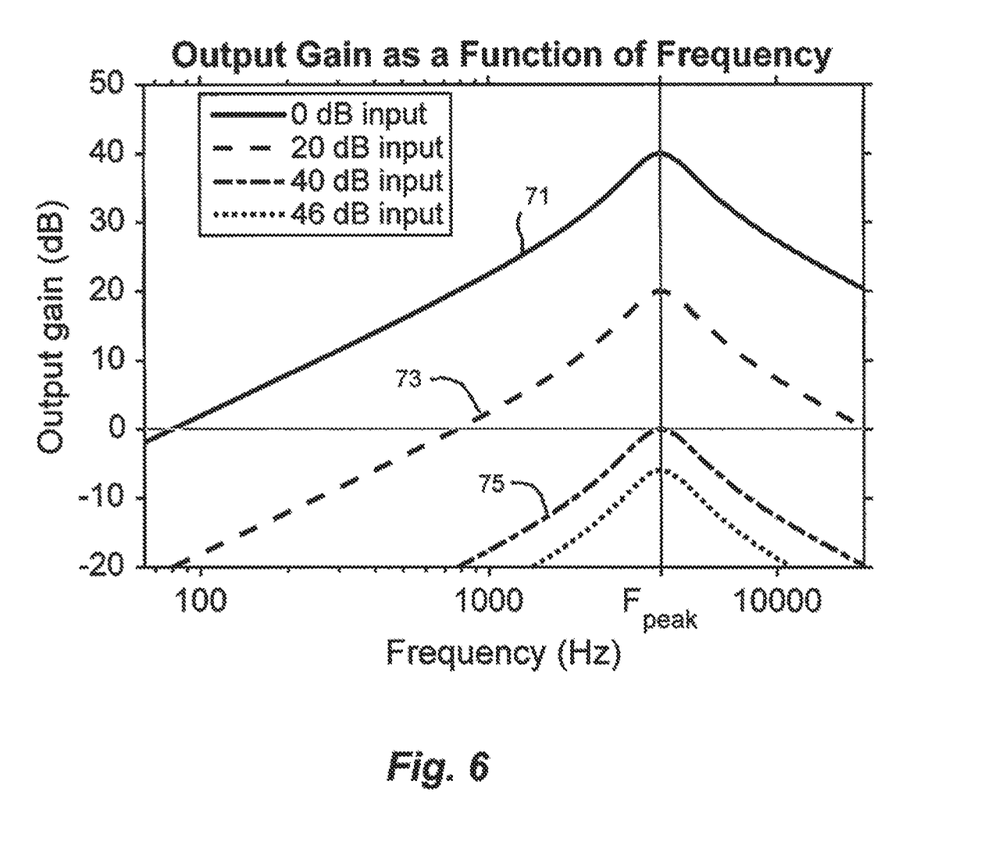
FIG. 6 shows how the output gain produced by a hearing aid decreases as the input sound pressure level rises. The gain is centered around a hypothetical peak frequency $F_{peak}$, where threshold compensation is needed.

In FIG. 6, threshold compensation is shown schematically for one frequency band using a band-pass filter with a peak frequency ($F_{peak}$) of 4 kHz. Such a filter corresponds to a typical noise-induced hearing loss of 40 dB at 4 kHz. The type of earpiece doesn't matter in this example, as long as the transparency sound fully compensates the insertion effect of the earpiece. For a flat input signal of 0 dB SPL, the output sound at 4 kHz (curve 71) is boosted by 40 dB, making those frequencies now audible to the user. Other parts of the frequency spectrum, already audible, aren't amplified. At the higher input levels of 20 and 40 dB SPL, it can be seen that the output gain (represented by curves 73 and 75 respectively) is progressively reduced so that the total output stays between 40 and 46 dB SPL. The output level is the sum of the LD (amplified) path (input level+gain) and the LI path; in the case of the 40 dB SPL input at $F_{peak}$, the output level is (40 dB SPL+0 dB gain)+40 dB SPL=46 dB SPL, assuming that both signals are fully coherent and have zero delay between them. Once the input level reaches 46 dB SPL, the chosen cut-off level for this example, the hearing aid provides only 2 dB amplification at 4 kHz: the combined output sound level is 48 dB SPL, only 2 dB above the cut-off level. At input levels above the cut-off level, the transparency sound will be perceived by the wearer without substantial additional gain. The example just described in FIG. 6 uses a linear gain function, as described in FIG. 8. In this example, the incoming sound producing the input signals for processing are considered to be static, with loudness and crest factor that don't vary in time. When amplifying soft sounds, the phase delay of the filter is acceptable to the user and audibility for low level speech and music is greatly improved.

Figure 7A:
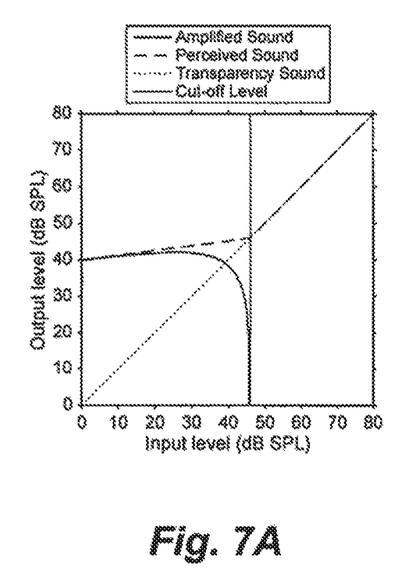
FIG. 7A shows the sound level, at one frequency, as a function of the input level for the perceived, amplified, and incident sound for one kind of gain curve.
Figure 7B:
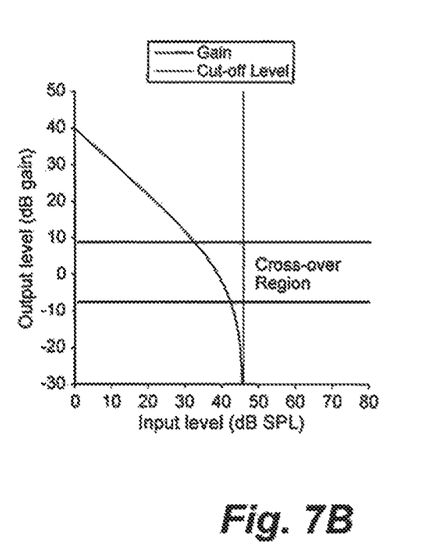
FIG. 7B shows the output gain, at one frequency, required to fit the perceived sound curve shown in FIG. 7A.
Figure 8A:
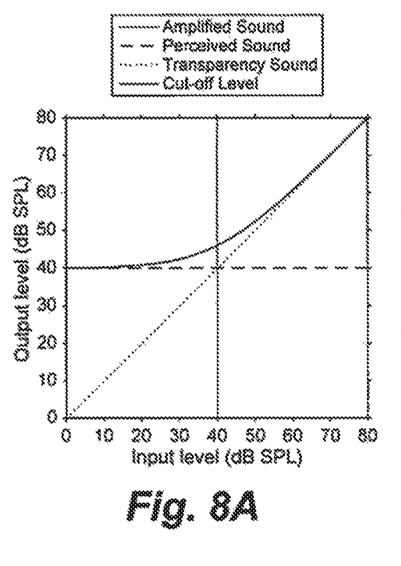
FIG. 8A shows the output sound level, at one frequency, as a function of the input level for the perceived, amplified, and incident sound, according to a second gain curve.
Figure 8B:
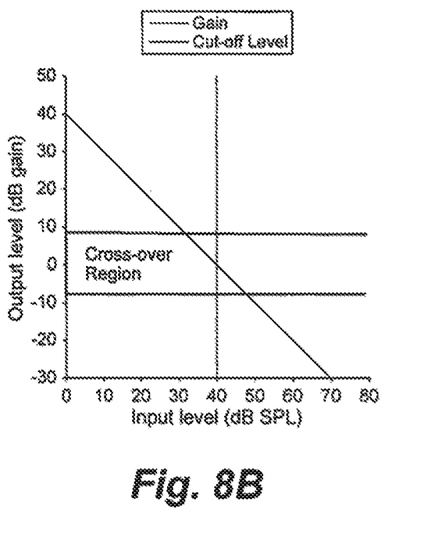
FIG. 8B shows the output gain, at one frequency, required to fit the perceived sound curve shown in FIG. 8A.

FIG. 7A shows the how the absolute levels of the three different sound paths change as a function of input level. Shown in FIG. 7B is the filter gain required to meet the perceived sound level shown in 7A. At low input sound levels (below approximately 10 dB for this example), the sound arriving at the eardrum and ultimately the perceived sound is seen to be dominated by the amplified sound. In this low input region, the gain of the filter is seen to decrease almost linearly with input level. Above this region is a "cross-over region" where the difference between amplified and transparency sound is less than about 8 dB. At levels within this cross-over region, both transparency and amplified sound contribute significantly to the perceived sound arriving at the eardrum. As a result, there can be a desirable deviation from linearity in the gain function within this region. This deviation in the cross-over region can be seen in FIG. 7B. Nonetheless, to prevent perceptual artifacts in the cross-over region, changes in the gain function should be gradual. That is, it should be monotonically decreasing, without discontinuities and smooth in the mathematical sense, with continuous derivatives. Effectively, such a well-defined gain function maps similar input levels to similar output levels; a small change in input level causes a small change to the output level. While as shown in FIG. 7B the optimal gain function is nonlinear in the cross-over region, it should be noted that a linear gain function (or a step-wise linear one) is also effective and may be easier to implement, as shown in FIGS. 8A and 8B.

Figure 9:
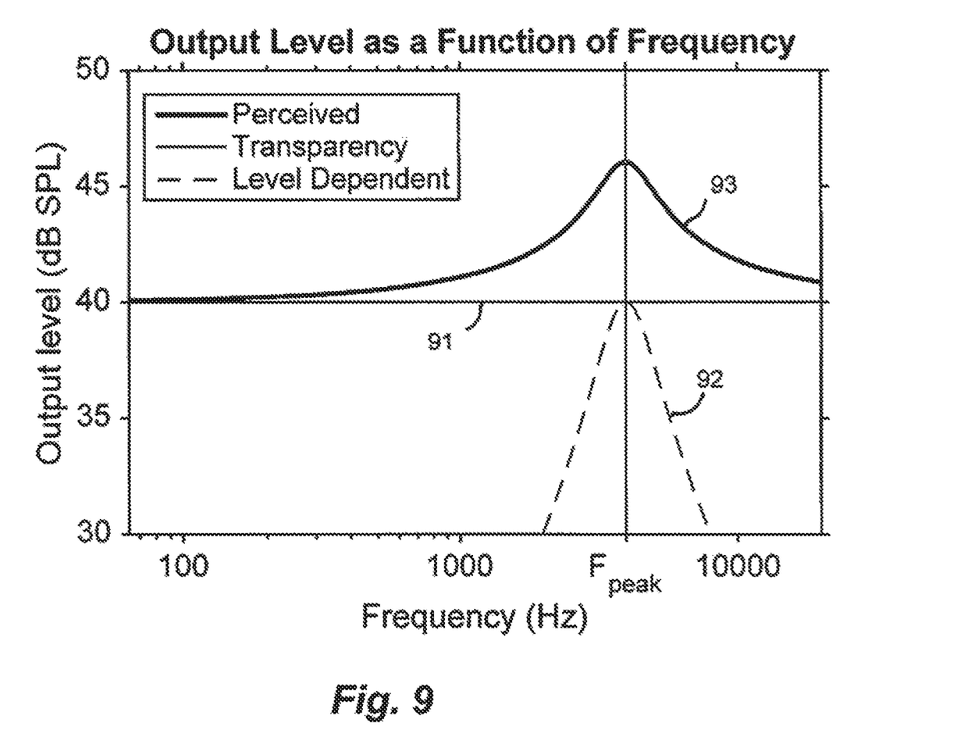
FIG. 9 shows how the incident and amplified sounds might sum at the ear drum for an input sound level right at the cross-over point.

FIG. 9 shows the transparency sound (curve 91) and LD sound (curve 92) and their summation (curve 93) at the point where the two sounds are equal in level (i.e., in the cross-over region). In the cross-over region, the phase and delay characteristics of the LD sound are particularly important in order for the two signals to sum coherently. If the phase difference between the LD and LI sound is 180° at any frequency, destructive interference will result in an attenuation that will be readily perceived by the user. The phase deviations preferably approach zero gradually as the filter gain decreases. As with the amplified sound pressure level, if the phase changes dramatically between slight changes in input level, it will create an artifact that can be noticed by the user.

Figure 10:
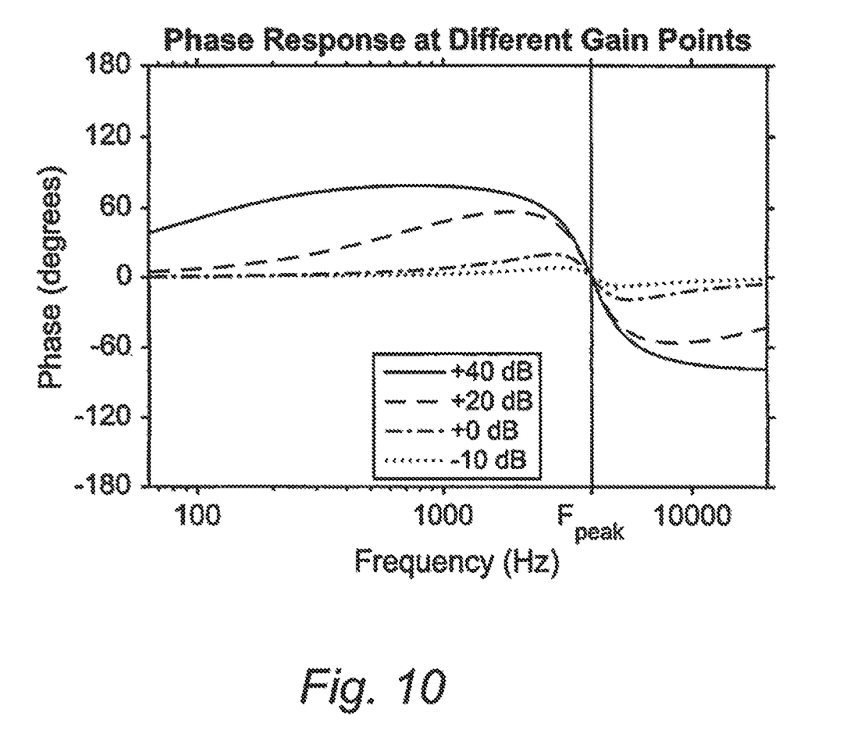
FIG. 10 shows how the phase response of the amplified path is attenuated as the output gain decreases, using the same gain levels as FIG. 5.

One way to avoid unacceptably large and perceptible phase changes with small changes in input level is illustrated in FIG. 10, which shows the phase perturbation or response slowly decreasing to zero as the input level rises and the LD gain decreases. As the gain decreases below zero, the phase response also decreases. For example, at 0 dB gain the phase response is smaller than at +20 dB gain. At −10 dB, there is virtually no phase response. Although filters that provide gain necessarily introduce a phase shift, this shift can be minimized by selecting an appropriate filter implementation (e.g., minimum phase). By reducing the phase response of the LD path, the chance of destructive interference upon summing with the LI path is also reduced.

One exemplary way to fit the LD filter parameters to a user's hearing loss is now described for a single frequency band. Assume the user has a tone-detection threshold of 60 dB SPL at this frequency. The maximum gain provided by the hearing aid is used for input levels far below the threshold; assume the hearing aid can provide 40 dB gain before feedback occurs. Now for an input signal at 20 dB SPL, the sound is amplified to 60 dB, right at threshold. The LD filter's cut-off frequency is set to 60 dB SPL, so that when the input level reaches 60 dB SPL, the LD filter has a gain of 0—amplified sound level equals incoming sound level—and the ear drum perceives a level of 66 dB SPL. At levels above this, the amplified sound drops further in level, and the output level becomes substantially linear.

An alternative way to set this filter would be to let the input/output gain have a slope of 0.25, which is equivalent to a ratio of 4:1; the input needs to increase by 4 dB for the output to increase by 1 dB. The gain curve would have a slope of 0.75 in this case. This would be useful for a conductive hearing loss, where loudness grows more gradually above the detection threshold. In this case, the cross-over region is both larger and occurs at a higher input level.

Other characteristics of the LD filters are the dynamic properties of each filter. These include the attack and release times, which are the time required for a filter to fully engage as the loudness of incident sound rises above the person's threshold of audibility and to fully disengage as the loudness of incident sound falls below this threshold. By employing dynamic control, (graphically represented by block 24 in FIG. 1), the attack and release times can be set such that sudden loud events aren't amplified, requiring a fast attack time, and such that soft sounds following a loud event remain audible, which requires a moderately fast release time. If either parameter is too long or too short, there will be tone coloration and noticeable level fluctuation; if the release time is too short, pumping artifacts will be noticed. The values of the dynamics will likely depend on the user's particular hearing loss and subjective feedback from the user during the fitting process. Generally, the filter attack time would suitably be set somewhere between about 15 microseconds and about 10 milliseconds, and preferably less than about 1 millisecond. The filter release time would preferably be in a range of about 200 microseconds to 30 milliseconds. These dynamics would most suitably be set by the manufacturer or trained professional.

While the hearing aid described above is a single channel device for one ear, it shall be understood that multiple frequency channels could be used, or a combination of two such devices for both ears. In such a case, the combination could share a physical enclosure for the electronics and a battery, but each ear would require its own ear piece, and preferably each ear would have its own a dedicated microphone and coherent gate. Separate microphones are recommended to preserve binaural cues, which are different at each ear. The LD filters will preferably be set independently for each ear because hearing loss may differ between ears. The microphones will preferably be worn as close to the ear as possible.

The other important parameter of the hearing aid is latency, the time between when the incident sound arrives at the microphone and leaves the loudspeaker. This delay needs to be kept as small as possible, ideally less than 1 millisecond. Delays longer than approximately 5 milliseconds also create artifacts of coloration, while delays longer than 1 millisecond affect sound localization cues. Thus, preferably, the latency introduced by the LD filter section 15 of the signal processor illustrated in FIG. 1 will be less than 1 millisecond. The latency requirement is most stringent for an open-ear device, where the direct sound is significant, and for unilateral hearing aids fit to a single ear. For open-ear devices, a long latency will result in combing at some frequency: a latency of 1 ms produces combing at 500 Hz and all harmonics, while a latency of 100 μs produces combing at 5000 Hz. For a unilateral hearing aid, a longer latency will disturb the interaural timing differences (ITDs), the difference in time of arrival that the brain uses to localize a sound source: the maximum ITD for humans is around 180 µs.

In order to realize the benefits of the above-described processing scheme, the microphone and loudspeaker should be capable of reproducing the audio signal with sufficient fidelity. The equal-phase response of the signal processor will not be realized unless both the input and output transducers are substantially linear; that is, unless they have a substantially flat phase response and low harmonic distortion (preferably less than 1%) at the loudest expected output level.

Figure 11:
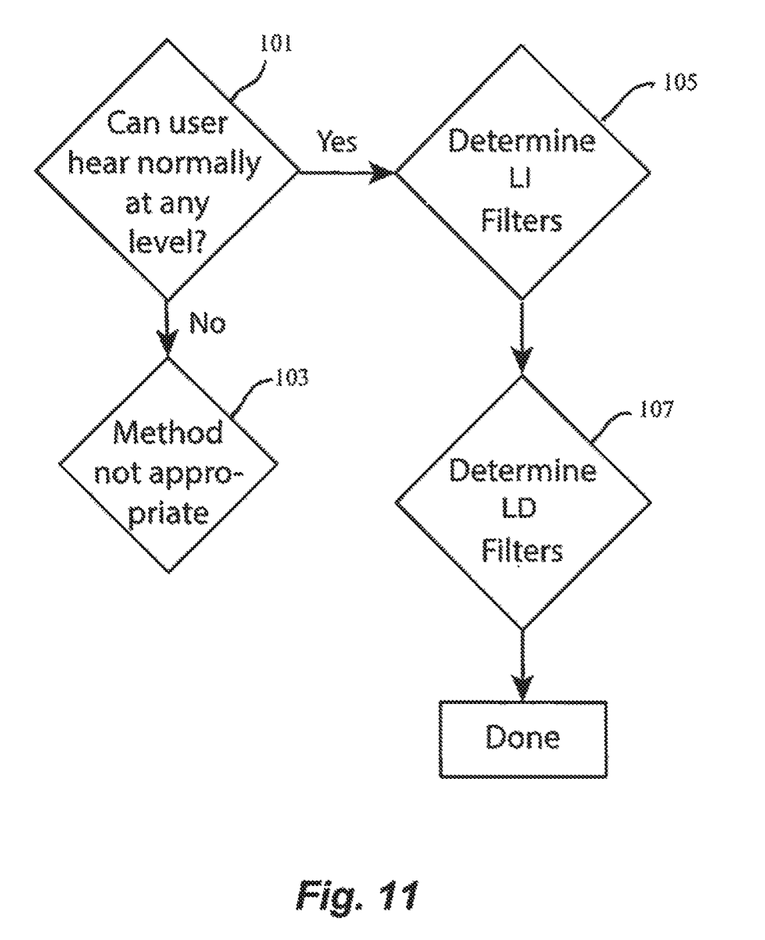
FIG. 11 is a flow chart illustrating the method of the invention.

FIG. 11 is a block diagram illustrating the general fitting methodology of the invention when applied to fitting a hearing aid worn by a user with hearing loss, and particularly when fitting a hearing aid as described above. First, as represented by block 101, it must be determined if the user can hear normally at any level. If the answer is no, the fitting method is not appropriate for this particular person (block 103). If, on the other hand, the answer is yes, the parameters for the transparency filters need to be determined next (block 105). As described above, the filter parameters can be determined by subjective feedback from the user or can be determined by direct measurement.

Once the transparency filter parameters are set, the parameters for the LD filters must be determined (block 107) for the user's particular hearing loss. This determination can also be made subjectively using feedback from the user. The steps for determining the filters can be done in an any order; that is, the LD filter parameters could be determined first, followed by the step of determining the LI filter parameters.

While the invention has been described in detail in the foregoing specification, it is not intended that the invention be limited to such detail, except as necessitated by the following claims.

We claim:

1. A hearing aid for compensating for the loss of hearing in a user's ear, wherein the hearing loss is characterized by an elevated tone detection threshold within one or more bands of frequencies, said hearing aid comprising:
    an input microphone for picking up sound incident on the user's ear and converting it to an electrical audio signal input,
    an earpiece having a loudspeaker, said earpiece being positionable within the user's ear and said loudspeaker producing sound perceived by the user of the hearing aid, and
    a signal processor for processing the electrical audio signal input from said microphone prior to the electrical audio signal input reaching the loudspeaker of the earpiece, said signal processor having a level-dependent signal path and a linear level-independent signal path for producing a signal input to the loudspeaker,
    wherein, in the linear level-independent signal path, the signal processor is configured to compensate for insertion loss caused by the presence of the earpiece in the user's ear and to produce transparency sound at all incoming sound levels,
    wherein the level-dependent signal path is configured to introduce level-dependent gain in the signal path within the one or more frequency bands where the user experiences hearing loss that produces amplified sound in each such frequency band only when the incoming sound has a sound level substantially at or below the user's tone detection threshold within such frequency bands, and
    wherein at least about and above the user's tone detection threshold the level-dependent signal path is further configured to decrease the gain introduced in the level-dependent signal path with an increase in the audio signal input from the microphone.

2. The hearing aid of claim 1 wherein said earpiece is configured to provide a closed ear hearing aid wherein, above the user's tone detection threshold, substantially all the sound delivered to the eardrum is provided through the linear level-independent signal path of the signal processor.

3. The hearing aid of claim 1 wherein said earpiece is configured to provide an open ear hearing aid that provides a direct sound path through the earpiece for sound to pass without substantial attenuation, and wherein a portion of the sound delivered to the eardrum is provided through the linear level-independent signal section of the signal processor and a portion is delivered through the direct sound path of the earpiece, and wherein, above the user's tone detection threshold, substantially all the sound delivered to the eardrum is provided through the linear level-independent signal section of the signal processor and the direct path of the earpiece.

4. The hearing aid of claim 1 further comprising means for converting incident sound to a digital audio signal, and wherein said signal processor is a digital signal processor.

5. The hearing aid of claim 1 wherein the level-dependent gain introduced in the level-dependent signal path decreases monotonically as the audio signal input from the microphone increases.

6. A hearing aid for compensating for the loss of hearing in a user's ear, wherein the hearing loss is characterized by an elevated frequency dependent tone detection threshold within one or more bands of frequencies, comprising:
    an input microphone for picking up incoming sound and converting it to an electrical audio signal input,
    an earpiece having a loudspeaker, said earpiece being positionable within the user's ear, and
    a signal processor for processing the electrical audio signal input from said microphone prior to the electrical audio signal input reaching the loudspeaker of the earpiece, said signal processor having a level-dependent filter section and a level-independent filter section,
    wherein the level-independent filter section compensates for the presence of the earpiece in the user's ear to produce transparency sound at all incoming sound levels, and
    wherein the level-dependent filter section introduces level-dependent gain in the hearing aid that depends on the level of the incoming sound within the one or more frequency bands where the user experiences hearing loss, the level-dependent filter section producing amplified sound within the one or more frequency bands where the user experiences hearing loss that sums with the transparency sound produced by the level-independent filter section, and
    wherein at least about and above the user's tone detection threshold the level-dependent filter section is further configured to decrease the gain introduced by the level-dependent filter section as the audio signal input from the microphone increases.

7. The hearing aid of claim 6 wherein the level-dependent gain introduced by the level-dependent filter section decreases monotonically as the audio signal input from the microphone increases.

* * * * *